United States Patent [19]

Bittman et al.

[11] Patent Number: 5,465,729
[45] Date of Patent: Nov. 14, 1995

[54] METHOD AND APPARATUS FOR BIOFEEDBACK

[75] Inventors: Barry B. Bittman, Meadville, Pa.; Jeffrey R. Cram, Nevada City, Calif.

[73] Assignee: Mindscope Incorporated, Meadville, Pa.

[21] Appl. No.: 194,260

[22] Filed: Feb. 10, 1994

Related U.S. Application Data

[62] Division of Ser. No. 850,673, Mar. 13, 1992, Pat. No. 5,343,871.

[51] Int. Cl.$^6$ ............................................. A61B 5/0482
[52] U.S. Cl. ............................................. 128/732; 128/700
[58] Field of Search ..................................... 128/731, 732, 128/733, 734, 700

[56] References Cited

U.S. PATENT DOCUMENTS

| | | | |
|---|---|---|---|
| 3,837,331 | 9/1974 | Ross . | |
| 3,855,998 | 12/1974 | Hidalgo-Briceno . | |
| 3,875,930 | 4/1975 | Silva et al. . | |
| 3,916,876 | 11/1975 | Freeman . | |
| 3,942,516 | 3/1976 | Glynn et al. . | |
| 3,967,616 | 7/1976 | Ross . | |
| 3,978,847 | 9/1976 | Fehmi et al. . | |
| 4,056,805 | 11/1977 | Brady . | |
| 4,140,997 | 2/1979 | Brady . | |
| 4,354,505 | 10/1982 | Shiga . | |
| 4,461,301 | 7/1984 | Ochs . | |
| 4,632,126 | 12/1986 | Aguilar | 128/732 |
| 4,665,926 | 5/1987 | Leuner et al. | 128/716 |
| 4,683,891 | 8/1987 | Cornellier et al. | 128/630 |
| 4,776,323 | 10/1988 | Spector . | |
| 4,823,808 | 4/1989 | Clegg et al. | 128/773 |
| 4,883,067 | 11/1989 | Knispel et al. | 128/732 |
| 4,896,675 | 1/1990 | Ohsuga et al. | 128/671 |
| 4,919,143 | 4/1990 | Ayers | 128/732 |
| 4,928,704 | 5/1990 | Hardt | 128/732 |
| 4,932,880 | 6/1990 | Kotick et al. | 128/715 |
| 4,984,158 | 1/1991 | Hillsman | 364/413.04 |
| 5,024,235 | 6/1991 | Ayers | 128/732 |
| 5,036,858 | 8/1991 | Carter et al. | 128/732 |
| 5,076,281 | 12/1991 | Gavish | 128/721 |

OTHER PUBLICATIONS

Manual (excerpt) by J&J Engineering, Inc.
Tortoise and Hare Instructions.
Alps Animation Instructions by Biocomp.
Advertisement for IBVA biofeedback system by Psychic Lab, Inc.
Pamphlet entitled "Video Interface For Biofeedback Equipment Systems" by Nebulae Productions.

*Primary Examiner*—William E. Kamm
*Assistant Examiner*—Scott M. Getzow
*Attorney, Agent, or Firm*—Webb Ziesenheim Bruening Logsdon Orkin & Hanson

[57] ABSTRACT

A method and apparatus for mediating a biofeedback session with a human subject in which measurements of electrophysiological quantities are used to control the presentation to the subject of a series of prestored audio-visual sequences of varying levels of clarity resident on a direct-access video storage device. The sequences are real scenes designed to induce a desired psychological state when viewed. As the subject succeeds in altering his physiological parameters, the clarity of the presented image and sound improve as an indication of success. By using the invention, the subject develops a conditioned response to the scenes and is able to control his physiological parameters even when away from the apparatus by remembering the audio-visual sequences used during treatment.

11 Claims, 2 Drawing Sheets

Microfiche Appendix Included
(2 Microfiche, 93 Pages)

(2 Microfiche, 93 Pages)

METHOD AND APPARATUS FOR BIOFEEDBACK

This is a divisional of application Ser. No. 07/850,673 filed on Mar. 13, 1992 now U.S. Pat. No. 5,343,871.

Two microfiche appendices are provided. Microfiche Appendix A comprises 46 frames on microfiche 1 of 2. Microfiche Appendix B comprises 56 frames on microfiche 2 of 2.

BACKGROUND OF THE INVENTION

1. Field of the Invention

This invention relates to a method of mediating a biofeedback session with a human subject in which measurements of certain of the subject's electrophysiological parameters are used to control the presentation to the subject of a series of prestored audio-visual sequences of varying levels of clarity or perspective to provide targets whose viewing induces in the subject a desired psychological state.

2. Description of the Prior Art

Biofeedback is a process in which electrodes are connected to a human subject to monitor electrophysiological parameters such as heart rate, electroencephalographic signals and galvanic skin resistance. These signals are converted to a visual or audio display that can been seen and/or heard by the subject, who attempts to alter the parameters using the display as a guide to his progress. If it is desirable to reduce blood pressure, for example, the display may consist of a bar graph indicating the magnitude of the pressure. If the subject is successful in lowering his blood pressure, he will see the size of the bar diminish and will thus know he is making progress.

Traditional biofeedback methods employ such mechanisms as analog meters, computer-generated displays, targets shown in cross-hairs, acoustic tones and audio beat frequencies to indicate to the subject the values of the parameters being monitored.

Biofeedback is commonly performed by a biofeedback technician, who directs the subject verbally to achieve a state of calm by coaching him to develop a mental image of a relaxing scene. Unfortunately, it can be difficult to relax during such a session because the subject is forced to concentrate on a computer display or audio tone to gauge his progress. That is, the result or display viewed by the subject is not in itself calming, and may actually interfere with the desired objective.

Biofeedback can be used to treat migraine and tension headaches, pain disorders such as temporomandibular joint dysfunction (TMJ) and myofascial syndromes, musculoskeletal tension, hypertension, anxiety and panic disorders, asthma, dyspepsia, and other conditions that can be controlled by reducing muscular tension, inducing a state of calm or stabilizing autonomic function. Biofeedback can be used both for treatment and prevention of such syndromes.

Biofeedback devices and methods comprising visual displays are known in the prior art. Ross U.S. Pat. Nos. 3,837,331 and 3,967,616 teach use of a "transducing means" for exhibiting sensory signal output to the human subject, which may include a matrix of numbered lamps, slides projected on a screen, or an audible chime. Hidalgo-Briceno U.S. Pat. No. 3,855,998 discloses an entertainment device that monitors electrophysiological parameters of a human subject and presents "audio-visual stimulation" comprising passages of music, flashing lights or projected images intended to place the subject in a desired psychological state. The Hidalgo-Briceno invention, while it receives electrical signals from the subject, is not a biofeedback device because the subject is not guided by stimuli to modify his own physiological parameters. Cornellier et al. U.S. Pat. No. 4,683,891 teaches use of a visual display to indicate the values of a subject's physiological parameters at the point where stress is induced during performance of a goal-oriented task.

A number of prior art biofeedback devices employ purely audio feedback to the subject. Silva et al. U.S. Pat. No. 3,875,930 teaches using a fixed audio signal that decays to silence as an indication that the desired brainwave waveform has been achieved. Spector U.S. Pat. No. 4,776,323 teaches playing sounds through headphones to induce relaxation in a subject for the purpose of creating a calm state that can then be interrupted by high-amplitude noises to cause stress. Knispel et al. U.S. Pat. No. 4,883,067 teaches a method of transforming brainwave activity into musical sound, which is fed back to the subject via headphones.

Numerous prior art devices combine audio and visual feedback. Glynn et al. U.S. Pat. No. 3,942,516 teaches simultaneous monitoring of a plurality of electrophysiological parameters to produce a single audio-visual output for feedback. Fehmi et al. U.S. Pat. No. 3,978,847 teaches using audio tones and a light that increases in amplitude and stroboscopic frequency as the frequency of the subject's brainwaves increases. Clegg et al. U.S. Pat. No. 4,823,808 teaches a method for treating eating disorders by measuring parameters of the gastrointestinal tract and providing indications of gastric activity by visual and audio means, as by amplifying stomach noises. Ohsuga et al. U.S. Pat. No. 4,896,675 teaches providing graphs of physiological parameters and simultaneously generating a sound pattern to be used by the subject to control his rate of respiration. Ayers U.S. Pat. Nos. 4,919,143 and 5,024,235 teach a sound and light box in addition to graph waveforms as output from a biofeedback system. Hardt U.S. Pat. No. 4,928,704 teaches combining tone feedback with display of digital data to the subject. Hillsman U.S. Pat. No. 4,984,158 teaches auditory prompts and use of visual graphs for instructing subjects to use a metered dose inhalation system. Carter et al. U.S. Pat. No. 5,036,858 teaches use of light goggles and headphones to convey beat signals to a subject indicative of how much his brainwave frequency differs from a desired frequency. Gavish U.S. Pat. No. 5,076,281 teaches using synthesized sound patterns and optical effects indicative of parameters of biorhythmic activity.

Freeman U.S. Pat. No. 3,916,876 teaches measurement of muscle tension in two selected muscles while the subject watches electrical meters displaying the tension measurements and other quantities derived from them. There is no audio or visual feedback other than meter readings.

Brady U.S. Pat. Nos. 4,056,805 and 4,140,997 disclose a video display comprising a matrix of colored lights that is controlled in response to brainwaves. Brady's invention does not comprise a biofeedback system, but is directed to conveying a visual indication of a subject's response to sound, particularly music. Shiga U.S. Pat. No. 4,354,505 teaches measurement of the length of time a subject has remained in a relaxed state by displaying numerals indicative of the said length. Ochs U.S. Pat. No. 4,461,301 teaches display of numerical indications dependent on the values of monitored electrophysiological parameters. Leuner et al. U.S. Pat. No. 4,665,926 teaches a system for measuring a person's relaxation state, but in which displayed information is not fed back to the subject but is instead monitored by a technician.

It is a drawback of prior art biofeedback devices and methods that the feedback provided to the subject is merely a display of values of physiological parameters or an indication of how successful the subject has been in achieving his goal. They do not provide a target, desirable in itself, to assist in the attainment of success. In fact, the prior art devices utilize feedback means that can actually interfere with the desired objective by forcing the subject to concentrate on a wave tracing, flashing light or blip on an oscilloscope screen in order to gauge his progress. In prior art methods, the subject must generally be coaxed by an assistant into imagining a relaxing scene or locale in order to alter his electrophysiological responses.

The following are objects of the present invention:

1. To improve the efficacy of biofeedback by eliminating dependence on stress-inducing visual or audio targets on which the subject must concentrate.

2. To determine an effective weighted combination of physiological potentials for a given subject that can be used in conditioning biofeedback response.

3. To monitor and record a subject's progress through one or more biofeedback treatments by storing and reporting data concerning the subject's responses on a digital computer so that the combination of physiological potentials monitored can be altered to maximize the effectiveness of the treatment.

4. To provide a means by which a subject's success in controlling his physiological potentials causes presentation of a graded sequence of pleasant scenes of successively greater video and audio clarity.

5. To combine conventional biofeedback devices with a videodisc to permit the presentation of selected image sequences in arbitrary order as a way of rewarding the subject for positive psychological responses.

6. To train the subject through biofeedback to induce self-relaxation subsequent to a training session without having to rely on a machine for audio-visual response.

7. To develop a conditioned response on the part of a subject so that he can induce in himself a desired psychoneurological state by recalling to memory one or more prestored audio-visual scenes.

SUMMARY OF THE INVENTION

Accordingly, we have invented a biofeedback system in which the feedback provided to the subject is itself calculated to induce the desired state, eliminating the need for the subject to imagine a nonexistent scene. The apparatus comprises (1) a high-quality display device, preferably a high-resolution television screen and high-fidelity audio system; (2) a playback device capable of playing back realistic prestored audio-video sequences quickly and in arbitrary order, preferably a laser disc player; and (3) a digital computer to monitor bioelectric signals and control the display device and the playback device. The apparatus is used in conjunction with a conventional set of biofeedback electrodes and associated amplifiers and analog-to-digital converters.

The apparatus monitors and records such electrophysiological parameters as, among others, (1) electromyographic (EMG) signals; (2) galvanic skin resistance (GSR); (3) electroencephalographic (EEG) signals; (4) skin temperature; (5) blood pressure (BP); and (6) heart rate (HR) or pulse. Signals indicative of these parameters are monitored by a computer capable of displaying prestored audio-visual scenes at varying levels of visual and acoustic clarity. The scenes themselves are of pleasurable images designed to induce relaxation, such as views of beaches with rolling surf, lush flower gardens, a sunset, a waterfall and the like. As the subject gradually attains the desired physiological state, the image becomes progressively enhanced. The "reward" to the subject for approaching the desired state is a successively clearer image, closer view or movement of an object. In this way, the subject is able to perform biofeedback without the distraction of prior art feedback indicators, which are not themselves relaxation inducing. Subsequent to the treatment, the subject is able to induce a relaxed state in himself by recalling the scenes used during treatment.

DETAILED DESCRIPTION OF THE INVENTION

Figure 1:
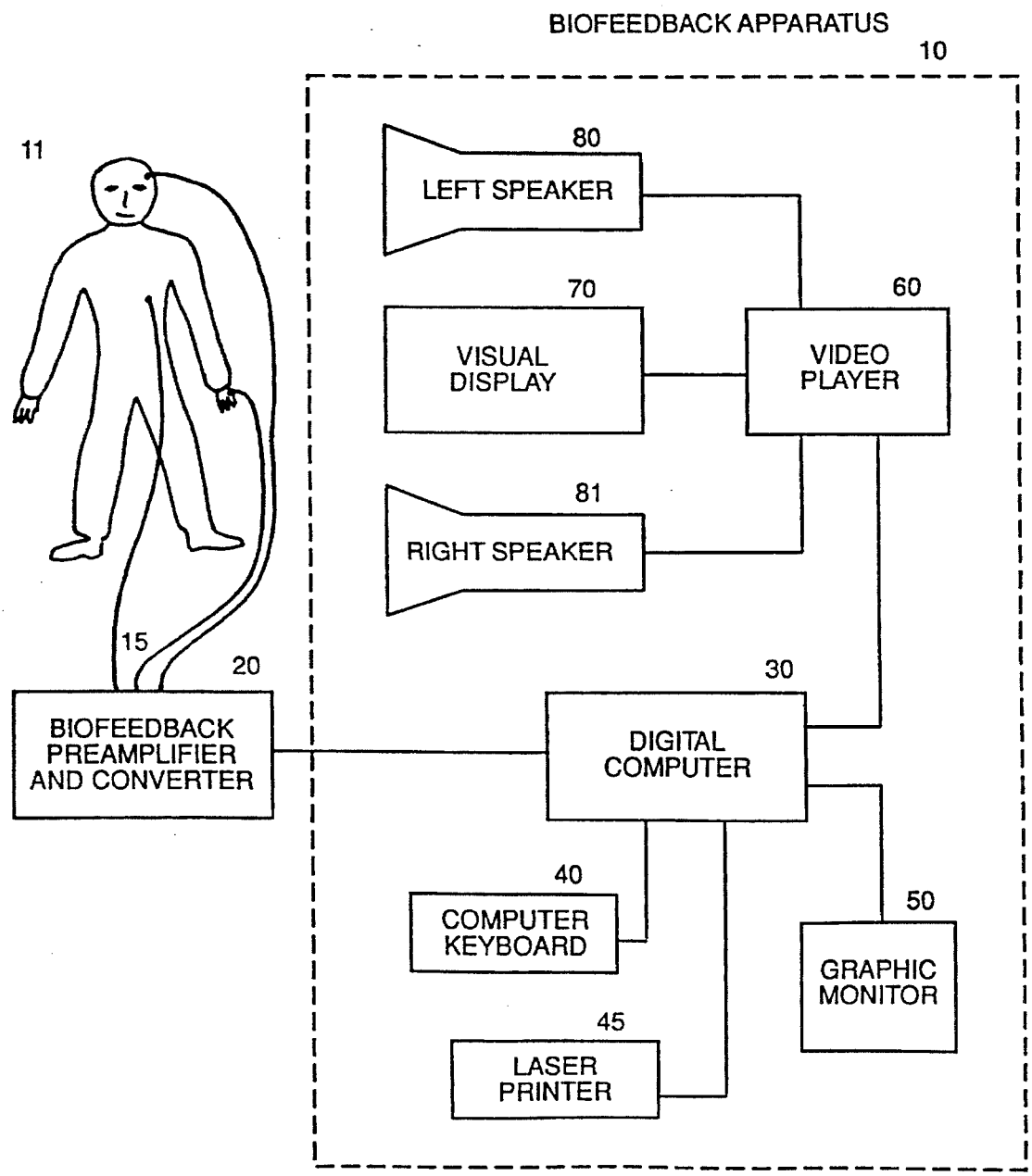
FIG. 1 shows a block diagram of the apparatus of the present invention.

Referring now to FIG. 1, which shows a block diagram of the apparatus of the present invention, comprising a biofeedback system 10. Electrodes 15 lead from human subject 11 into the input terminals of preamplifier and converter 20. Preamplifier and converter 20 contains preamplifiers and amplifiers and analog-to-digital converters to transform analog signals into digital outputs indicative of the magnitude of said analog signals. Preamplifier and converter devices of this type are well-known in the prior art. Examples of such devices are the Autogenics A-8000, the J&J -1-330 Modular System, and the SRS Orion 8600 and PRO Series Model 421. The digital output of preamplifier and converter 20 is connected to an input port of digital computer 30. In a preferred embodiment, digital computer 30 is compatible with an international Business Machines personal computer running the DOS operating system and preferably containing an Intel 386SX or higher microprocessor. A fast microprocessor is required, for example, to process EEG signals, which exhibit a high information rate. In a preferred embodiment, digital computer 30 includes a hard disk (not shown) for data storage, a keyboard 40 for entering commands, a printer 45, preferably a laser printer, for printing reports and a high-resolution graphic monitor 50 to display command menus and graphs of the subject's progress to the biofeedback technician. In a preferred embodiment, keyboard 40 has at least ten function keys, F1 through F10. An asynchronous serial port of computer 30 is connected to video player 60, whereby the player can be controlled by the computer. In a preferred embodiment, video player 60 is a laser videodisc player such as the Pioneer Model LD-V8000 and the connection to computer 30 is made with a Pioneer serial cable P/N CC-13. The Model LD-V8000 is capable of holding a video image while access to a different portion of the videodisc is being established. This eliminates blanking of the display device between selection, which is undesirable because it interrupts the concentration of the subject. Video player 60 need only be capable of directly and quickly accessing video sequences in arbitrary order on a video storage medium of sufficient capacity to conduct a session of sufficient duration that no reloading is required during a biofeedback session, which would cause interruption of treatment.

The video output of video player 60 is connected to video display 70, which is preferably a large screen television monitor having a resolution of at least 350 horizontal lines. The left and right stereophonic audio outputs of video player 60, respectively, are connected to left speaker 80 and right speaker 81. In an alternate embodiment, speakers 80 and 81 are integrated into a set of headphones worn by subject 11. In a further embodiment, video display 70 is a television set incorporating built-in speakers 80 and 81.

A manual describing the use of the system in the best mode known to the inventors j.s reproduced in microfiche Appendix A.

Figure 2:
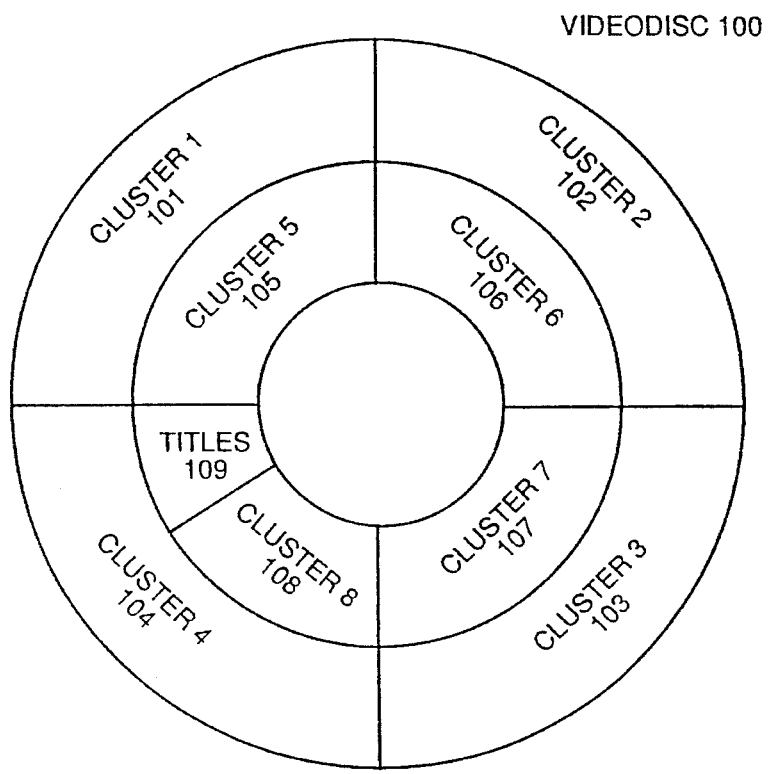
FIG. 2 shows a layout of clusters of audiovisual scenes on a videodisc of the type used in the present invention.

FIG. 2 shows the schematic layout of a typical videodisc used with the present invention. Videodisc 100 comprises eight clusters 101–108 and a title sector 109. The playing time of each of the clusters 101–107 is approximately 7.5 minutes. The playing time of cluster 108 is approximately 2.5 minutes. The playing time of the title sector is approximately 30 seconds. The playing time of the entire videodisc 100 is approximately one hour.

Videodisc 100 is removably inserted in video player 70. The videodisc contains title information and eight ordered sequences, or clusters, of information, each cluster comprising five segments containing related audio-visual scenes. The scenes are related in that they depict substantially the same subject matter but may differ in such respects as level of audio-visual quality, viewpoint from which the scenes were photographed or may show one or more objects in differing positions in each scene. The objective is to provide a graded sequence of scenes in which each is an improvement on the preceding scene in some respect; that is, each scene is more real or more desirable than its predecessor. Within each cluster, therefore, the five scenes are recorded at differing levels of "reality."

For example, a scene may be made more real to the subject by presenting it in progressively sharper focus, beginning with a blurry image and ending with a clear one. Alternatively, an object may be shown in a beginning scene at a great distance from the subject and in successive scenes shown coming closer and closer. A third method of changing the reality level is to show the object moving within the scene toward a natural goal, as the sun setting, an airplane landing, a climber reaching the top of a peak, a runner approaching the finish line of a race, and the like. The objective of these sequences is to provide the subject with a audio-visual objective that becomes better as the subject improves his physiological parameters.

A discrete level of reality is known as a Laser Video Reality Index (LVRI). The five levels are assigned the labels LVRI 1 through LVRI 5. LVRI 1 represents the highest level of reality; LVRI 5 represents the lowest level of reality. The subject is rewarded for favorable biofeedback response by being shown an audio-visual scene at a higher reality level (lower LVRI level). The purpose of using differing reality levels is to provide the subject with successive related image targets and to indicate to the subject by nondistracting means that biofeedback is succeeding. Because all of the scenes within a cluster are partially degraded versions of the same desirable image, the subject recognizes the target scene and anticipates improvement in the display, further inspiring his effort at biofeedback.

Negative feedback can be provided by decreasing the level of reality if the subject's physiological parameters move away from the desired direction. The present invention has divided reality levels into discrete steps so that the subject is not presented with a constantly fluctuating image on which attention or enjoyment would be difficult. For example, if the size of a viewed object were to change continually based on the subject's galvanic skin resistance, the subject would have no fixed target on which to gaze and would be distracted or disturbed by its incessant movement. By dividing the range of responses into discrete quanta, the subject is better able to concentrate on the scenes being presented.

During the use of the present invention, the human subject sees and hears only material designed to induce and lead the subject to the desired state. No objective indications of progress, such as graphs, meters, flashing lights, moving dots or other means used in prior art devices and which (1) cause distraction; and (2) do not provide the subject with a desirable mental image for later recall are here employed.

Figure 3:
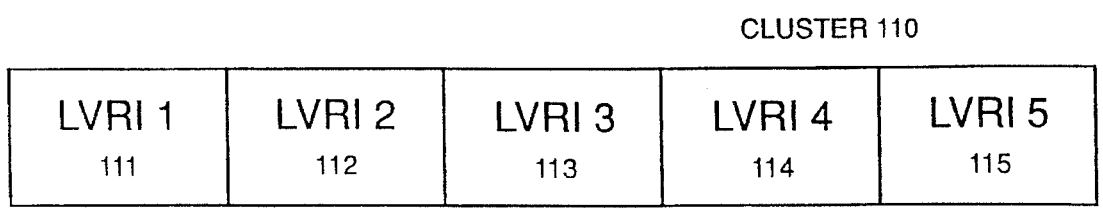
FIG. 3 shows the internal arrangement of a single cluster of audio-visual scenes on the videodisc of FIG. 2.

FIG. 3 shows a schematic layout of a typical cluster audio-visual scene. Cluster 110 comprises five LVRI segments 111–115 in order of reality index from highest (LVRI 1) to lowest (LVRI 5). The playing time of each LVRI segment is approximately 1.5 minutes. If the subject has not progressed during that time, the segment is automatically replayed or "looped."

The LVRI segments are created by capturing real scenes on videotape using high-quality commercial television equipment. Varying levels of clarity can be achieved by degrading the image during taping as explained below. After the segments are recorded on videotape, acoustic degradation and further video degradation can be performed in an editing studio. When all segments are of appropriate length and LVRI level, a master videotape is made from which a videodisc can be produced by known methods.

The scenes to be recorded on videodisc are chosen so that the audio-visual segments themselves both induce the desired psychological state in the subject and to provide memorable audio-visual images that the subject may bring to mind subsequent to the biofeedback session for therapeutic effect.

Audio-visual degradation must be performed in a way that allows the subject to focus his attention on a single scene to avoid distraction or confusion of physiological response. This can be achieved by utilizing one audio-visual scenario and successively reducing its quality. At all times, however, the goal scene is maintained in view, though it may be distant or fuzzy. The images representing the scene are presented to the subject in order of increasing clarity to serve as a reward for achieving desired response levels.

Video degradation to produce different LVRI levels can be accomplished by analog or digital means through (1) defocusing the image; (2) eliminating or reducing color; (3) zooming by magnifying or demagnifying the image; or (4) photographing objects in the scene in varying positions or states. In a preferred embodiment, video degradation is performed by analog means as the scenes are being recorded on the videotape from which a videodisc is later made. This is done by (1) defocusing by moving the focus ring on the video camera; (2) altering the apparent distance to the scene by zooming; (3) recording successive scenes in which an object progressively moves toward a goal, such as a series of images of the sun setting, with attendant colorful illumination of the sky; and (4) varying video color parameters such as hue and tint by adjusting analog controls. The analog method of video degradation is preferred because it appears more natural to the subject.

Audio degradation is accomplished by simultaneously (1) reducing the stereo separation of the left and right audio signals; (2) reducing the volume of the signals; (3) reducing the amplitude of the audio signal at or above selected frequencies (clipping); and (4) audio panning, which varies the extent to which sounds move from the left to right stereo channels and vice versa. Table 1 indicates how the first two of these parameters vary by LVRI in a preferred embodiment.

TABLE 1

Audio Degradation at Different LVRI Levels

| Reality Level | Stereo Separation | Cut at 3 kHz (decibels) | Rolloff at 5.5 kHz (decibels) |
| --- | --- | --- | --- |
| LVRI 1 | 100% | 0 | 0 |
| LVRI 2 | 75% | 3 | 3 |
| LVRI 3 | 50% | 6 | 6 |
| LVRI 4 | 25% | 11 | 12 |
| LVRI 5 | 0% | 18 | 20 |

Audio distancing, another method of obtaining differing LVRI levels, is accomplished by simultaneously reducing the stereo separation of the left and right audio signals and the overall amplitude of the audio signal. Table 2 indicates how these parameters vary by LVRI in a preferred embodiment.

TABLE 2

Audio Distancing at Different LVRI Levels

| Reality Level | Stereo Separation | Amplitude Reduction (decibels) |
| --- | --- | --- |
| LVRI 1 | 100% | 0 |
| LVRI 2 | 100% | 3 |
| LVRI 3 | 90% | 6 |
| LVRI 4 | 80% | 11 |
| LVRI 5 | 60% | 16 |

An example of the use of video degradation and enhancement is in behavior modification. By gradually exposing a phobic subject to a series of stressful scenarios, the subject can be rewarded via audio-visual feedback for generating a desired physiological response, the reward consisting of a change in the audio-visual template. For example, an acrophobic individual (one who fears heights) can be acclimatized to differing elevations under controlled conditions without actual risk by being shown a sequence of scenes taken at varying heights. The method is not restricted to achieving relaxation. A rehabilitation patient who is being trained to use certain muscles can be rewarded for exerting stress rather than relaxing.

An agoraphobe (one who fears being out in public) can be treated by presenting scenes commencing at home, gradually moving outdoors, a quiet street, an intersection, and then a mall or busy city block. As the subject relaxes, as monitored by the apparatus, the journey progresses. The subject becomes conditioned to associate relaxation with situations that formerly induced anxiety. Similar methods can be used to treat other phobias such as vertigo, reactive anxiety states or panic attacks.

Reduction of tension has been shown to reduce learning time for certain motor skills as typing, stenography and repetitive manufacturing activities. It also improves work efficiency and can assist athletes in preparing for competitive sporting events. The present invention is also useful in these applications.

A number of distinct audio-visual sequences can be recorded on a single videodisc and are available for selection by the biofeedback technician controlling the session.

The software used to control the apparatus of the present invention is listed in source code form in microfiche Appendix B. It is written in a programming language known as the BOS Protocol Programming Language implemented under the Biomedical Operating System (BOS), which is available for license from Stuart Enterprises, 11330 Southwind Court NE, Bainbridge Island, Wash. 98110. BOS supports popular biofeedback processors comprising electrodes, amplifiers and analog-to-digital converters, making it possible to connect the present invention to many types of standard biofeedback equipment. BOS and its programming language, in which the software of the present invention is written, are described in full in the publication, BOS Biomedical Operating System User's Manual, copyright 1990, published by Stuart Enterprises.

The invention can be used in the following manner. A physician evaluates the subject and determines the protocol to be used and the desired physiological objectives, based on which a series of scenes is chosen for presentation to the subject.

The subject does not see or interact with the system screen. The subject is presented only with audio-visual imagery so as to keep his attention focused on the treatment. The subject may even be placed in a room remote from the computer and other equipment, with only a television set to observe. This separation is particularly beneficial for subjects who experience anxiety in interacting with a computer.

During a first session with a human subject, a biofeedback technician explains the techniques that will be employed and explains the protocol and objectives. The technician then performs an initial evaluation to calibrate the subject's electrophysiological responses. In the initial evaluation, the subject is seated in a comfortable chair, with biofeedback electrodes in place, and shown a series of different high-quality audio-visual scene sequences, each lasting 90 seconds. Electrophysiological parameter measurements are recorded by the computer and reported in graphic and tabular form to the technician, who may select a sequence for viewing during later treatment sessions. The technician may also select one or more parameters whose values will be used to control changes in clarity levels in the chosen sequence.

For a treatment session, the technician places electrodes on the subject and inserts in the videodisc player a disc containing the scene sequence to be used during treatment. Of the several sequences that may be present on the disc, the particular one to be used can be chosen by the technician from a menu of choices presented on graphic monitor 50. The technician controls the apparatus by viewing the monitor and entering information through computer keyboard 40. During the session, the monitor displays graphically the values of the subject's electrophysiological parameters. The technician interacts with computer 30 through screens that appear on monitor 50. The screens, whose content and order is controlled by software in computer 30, provide menu choices that are selected by pressing one of the function keys F1 through F10. The technician may also be asked to enter textual or numeric information through keyboard 40.

The technician may choose the duration of the biofeedback session and the particular set of parameters to be recorded during the session. The parameters being recorded are not necessarily all used to control changes in LVRI level. The technician may choose, for each recorded parameter, whether it is to participate in LVRI changes, and, if so, what linear weight will be given to the parameter. That is, the function used to control LVRI changes is a linear combination (weighted average) of values of selected recorded parameters. The parameters that make up this function are called "linking parameters." For each linking parameter, the technician has the ability to scale the parameter by specifying the range of values, from "best" to "worst," that the parameter may assume. Values near "best" are associated with the most clear LVRI image (LVRI 1); those near "worst" cause the most distant, or fuzziest, LVRI image to be displayed (LVRI 5).

By adjusting the scaling of linked parameters in subsequent sessions, the technician may vary the degree of progress the subject must make in biofeedback before being rewarded with a clearer LVRI image. In beginning sessions, it may be desirable to reward the subject for only having made a small amount of progress in altering a parameter. As the subject becomes more skilled, the requirements can be adjusted so that more relaxation, for example, can be achieved for the same level of reward. Scaling information is presented on a graphical report so the technician can review the subject's attainment during the session and decide on the appropriate scaling for the next session.

When the session is complete (i.e. the preset session time has elapsed), the system produces printed reports and graphs for analysis by the technician and physician. These include the values of recorded parameters and LVRI level changes against time, in the form both of tables and plotted graphs. The technician also has the capability of annotating the reports from the keyboard. The annotations and a signature line in accordance with accepted medical record keeping practice appear on the printed reports, which are produced on laser printer 45.

The result of the session is that the subject has been made to relax and to associate the relaxation with the particular audio-visual sequence that was displayed. Furthermore, the sequence itself, as a result of the initial evaluation, is known to assist the subject in attaining the desired relaxation. The technician does not need to coach the subject to conjure up an imagined scene. The subject will be able, after one or more sessions, to induce himself into a state of relaxation outside of a moderated biofeedback session by remembering the particular audio-visual sequence. By using the present invention, the subject develops a conditioned biofeedback response.

The technician controls the system by interacting with it through a small number of screen displays, which are primarily menu-driven. The complete computer source code implementing these functions is given in Microfiche Appendix B.

The Initial Screen simply displays title information stored on videodisc 100 in title sector 109. The Main Menu Screen permits the choice of seven functions, each of which is invoked by depressing one of the programmed function keys F1 through F6 and F10 on computer keyboard 40. The Main Menu Screen functions are:

Main-F1. Demographics. This option invokes another screen permitting the technician to record biographical data, including the subject's name and other identifying information, for later report generation.

Main-F2. Initial Evaluation. This causes the computer to display to the technician the values of actual signals being received by the biofeedback electrodes 115 so the electrodes can be adjusted. It also presents the subject with a sequence of audio-visual displays so the technician can determine which scene on the videodisc produces the most favorable response from the subject.

Main-F3. Screen Selection. This permits a choice of the scene sequence to be used for the present biofeedback session, among those available on the videodisc that is currently mounted.

Main-F4. Control Screen. This screen controls the actual biofeedback session and itself provides eight programmed functions, discussed below.

Main-F5. Reports Screen. This invokes a screen to control report generation, including selection of report format, as discussed below.

Main-F6. Utilities Screen. This invokes the Disk Operating System (DOS) housekeeping functions, such as copying, formatting, etc.

Main-F10. End. This terminates the session.

The following functions are available on the Control Screen, which is invoked from the Main Menu by depressing the F4 key:

Control-F1. Session Time. Allows the technician to set the duration of the session.

Control-F2. Modalities. Allows selection of electrophysiological parameters to be recorded for this session.

Control-F3. LVRI Link. Establishes a relationship between electrophysiological parameters and the reality index progression for this session. The technician is able to choose which of the recorded parameters will actually be used to change LVRI levels and can assign relative weights to their importance.

Control-F4. Scaling. Allows setting of baseline levels and ranges for electrophysiological parameters.

Control-F5. Start/Stop. Begins and ends a biofeedback session and controls recording of parameters and output of reports.

Control-F6. Pause. Temporarily halts data recording to allow interruptions, such as for adjustment of electrodes.

Control-F7. Progress. Allows toggling between the Control Screen and the Progress Screen. The Progress Screen displays to the technician a graphic representation of the recorded parameters versus time so the progress of the subject can be monitored.

Control-F10. Main Menu. Returns to the Main Menu. This option cannot be selected until a session has been halted with the F5 key.

The following functions are available on the Video Screen, which can be invoked from the Main Menu by depressing the F6 (Utilities) key.

Video-F1. Help. Provides documentation of options.

Video-F2. Status. Indicates the position of the disc and slide door.

Video-F3. Open Slide Door. Opens the disc drawer on video player 60 so videodisc 100 may be inserted or removed therefrom.

Video-F4. Close Slide Door. Closes the disc drawer so that the disc can be read and a session can begin.

Video-F10. Return to Main Menu.

The following functions are available on the Reports Screen, which can be invoked from the Main Menu by depressing the F5 (Reports) key.

Report-F1. Graphs. Generates a line graph versus time for each modality selected in the Control Screen, which correspond to the electrophysiological parameters being monitored for this subject.

Report-F2. Tables. Generates a table of numerical values of each modality at discrete time steps throughout the session.

Report-F3. Progress Note. Invokes a word processor so the technician can introduce notes into the patient's medical record.

Report-F4. All Reports. Causes the system to produce all possible output reports for this session.

Report-F10. Return to Main Menu.

It will be evident to those skilled in the art that the invention is not limited to the details of the foregoing illustrative embodiment and that the present invention may be embodied in other specific forms without departing from the spirit or essential attributes thereof. The present embodiments are therefore to be considered in all respects as illustrative and not restrictive. The scope of the invention being indicated by the appended claims and rather than by the foregoing description and all changes which come within the meaning and range of the equivalency of the claims are therefore intended to be embraced therein.

We claim:

1. A method of altering the reality of the visual images and stereophonic audio sounds of a recorded audio-visual scene depicting objects, comprising the steps of:
   a) performing a plurality of operations from the group consisting of changing the focusing of the images, altering a color content of the images, altering an apparent distance to the objects in the images and altering a position of at least one object in the images; and
   b) performing a plurality of operations from the group consisting of altering a degree of stereophonic separation of the sounds, altering the audio volume of the sounds, altering an amplitude of at least one frequency component of the sounds above a selected frequency, moving an apparent acoustic position of at least one object by altering a relative audio amplitude contribution from said object to at least two channels of the stereophonic sound.

2. The method of claim 1 further comprising the step of:
   c) using the altered images and sounds in a biofeedback session.

3. A method of altering the reality of the visual images and stereophonic sounds of a recorded audio-visual scene depicting objects, comprising the steps of:
   a) performing a plurality of operations from the group consisting of changing the focusing of the images, altering a color content of the images, altering an apparent distance to the objects in the images and altering a position of at least one object in the images;
   b) performing a plurality of operations from the group consisting of altering a degree of stereophonic separation of the sounds, altering the audio volume of the sounds, altering an amplitude of at least one frequency component of the sounds above a selected frequency, moving an apparent acoustic position of at least one object by altering a relative audio amplitude contribution from said object to at least two channels of the stereophonic sound; and
   c) using the altered images and sounds in a biofeedback session with a subject by presenting said images and sounds to said subject in an order dependent upon a value of at least one electrophysiological parameter of the subject.

4. The method of claim 3 further comprising the step of:
d) controlling said biofeedback session including
   i) selecting at least one of said electrophysiological parameters to be monitored;
   ii) computing a weighted average of said values of said monitored parameters; and
   iii) repeatedly selecting one of said images and said sounds for exhibition to said subject based upon said weighted average.

5. A method of altering the reality of the visual images and stereophonic audio sounds of a recorded audio-visual scene depicting objects, comprising the steps of:
   a) performing a plurality of operations from the group consisting of changing the focusing of the images, altering a color content of the images, altering an apparent distance to the objects in the images and altering a position of at least one object in the images;
   b) performing a plurality of operations from the group consisting of altering a degree of stereophonic separation of the sounds, altering the audio volume of the sounds, altering an amplitude of at least one frequency component of the sounds above a selected frequency, moving an apparent acoustic position of at least one object by altering a relative audio amplitude contribution from said object to at least two channels of the stereophonic sound;
   c) using the altered images and sounds in a biofeedback session; and
   d) controlling said biofeedback session in which at least one electrophysiological signal is acquired from a subject and said images and sounds are presented to said subject in an order dependent upon a value of said at least one electrophysiological signal, said controlling including
   i) selecting at least one of said electrophysiological signals to be monitored;
   ii) computing a weighted average of said monitored signals; and
   iii) repeatedly selecting one said image and one said sound for exhibition to said subject based upon said weighted average.

6. A computer implemented method for controlling a biofeedback session in which at least two electrophysiological signals are acquired from a subject and versions of an audio-visual scene are exhibited to the subject, said versions having varying levels of reality, said method comprising the steps of:
   i) selecting a plurality of said signals to be monitored;
   ii) computing a weighted average of said monitored signals; and
   iii) repeatedly selecting one of said versions for exhibition to the subject based upon said weighted average.

7. A computer method for controlling a biofeedback session in which at least one electrophysiological signal is acquired from a subject and versions of an audio-visual scene are exhibited to the subject, said versions having varying levels of reality, said method comprising the steps of:
   i) selecting at least one of said signals to be monitored;
   ii) computing a weighted average of said monitored signals; and
   iii) repeatedly selecting one of said versions for exhibition to the subject based upon said weighted average, wherein said versions of said audio-visual scene are represented by the altering of the reality of the visual images and stereophonic audio sounds of a recorded audio-visual scene depicting objects including:

a) performing a plurality of operations from the group consisting of changing the focusing of the images, altering a color content of the images, altering an apparent distance to the objects in the images and altering a position of at least one object in the images; and b) performing a plurality of operations from the group consisting of altering a degree of stereophonic separation of the sounds, altering the audio volume of the sounds, altering an amplitude of at least one frequency component of the sounds above a selected frequency, moving an apparent acoustic position of at least one object by altering a relative audio amplitude contribution from said object to at least two channels of the stereophonic sound.

8. A computer controller for controlling a biofeedback session in which at least two electrophysiological signals are acquired from a subject and versions of an audio-visual scene are exhibited to the subject, said versions having varying levels of reality, comprising:

a) means for selecting a plurality of said signals to be monitored;

b) means for computing a weighted average of said monitored signals; and c) means for repeatedly selecting one of said versions for exhibition to the subject based upon said weighted average.

9. A computer controller for controlling a biofeedback session in which at least one electrophysiological signal is acquired from a subject and versions of an audio-visual scene are exhibited to the subject, said versions having varying levels of reality, comprising:

means for selecting at least one of said signals to be monitored;

means for computing a weighted average of said monitored signals; and means for repeatedly selecting one of said versions for exhibition to the subject based upon said weighted average, wherein said versions of said audio-visual scene are represented by the altering of the reality of the visual images and stereophonic audio sounds of a recorded audio-visual scene depicting objects including:

a) performing a plurality of operations from the group consisting of changing the focusing of the images, altering a color content of the images, altering an apparent distance to the objects in the images and altering a position of at least one object in the images; and b) performing a plurality of operations from the group consisting of altering a degree of stereophonic separation of the sounds, altering the audio volume of the sounds, altering an amplitude of at least one frequency component of the sounds above a selected frequency, moving an apparent acoustic position of at least one object by altering a relative audio amplitude contribution from said object to at least two channels of the stereophonic sound.

10. A computer implemented method for controlling a biofeedback session in which at least one electrophysiological signal is acquired from a subject and discrete versions of an audio-visual scene are exhibited to the subject, said discrete versions having varying discrete levels of reality, said method comprising the steps of:

i) selecting at least one of said signals to be monitored;

ii) computing a weighted average of said monitored signals; and iii) repeatedly selecting one of said discrete versions for exhibition to the subject based upon said average.

11. A computer controller for controlling a biofeedback session in which at least one electrophysiological signal is acquired from a subject and discrete versions of an audio-visual scene are exhibited to the subject, said discrete versions having discrete varying levels of reality, said computer controller comprising:

a) means for selecting at least one of said signals to be monitored;

b) means for computing a weighted average of said monitored signals; and c) means for repeatedly selecting one of said discrete versions for exhibition to the subject based upon said weighted average.

* * * * *